United States Patent
Kohama

(10) Patent No.: US 8,038,658 B2
(45) Date of Patent: Oct. 18, 2011

(54) SYNTHETIC RESIN NEEDLES AND SYNTHETIC RESIN COMPOSITION FOR NEEDLES

(75) Inventor: Hiromasa Kohama, Kanagawa-ken (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 436 days.

(21) Appl. No.: 11/992,383

(22) PCT Filed: Sep. 21, 2006

(86) PCT No.: PCT/JP2006/318738
§ 371 (c)(1),
(2), (4) Date: Feb. 25, 2009

(87) PCT Pub. No.: WO2007/037164
PCT Pub. Date: Apr. 5, 2007

(65) Prior Publication Data
US 2009/0312480 A1    Dec. 17, 2009

(30) Foreign Application Priority Data
Sep. 28, 2005    (JP) .................... 2005-281331

(51) Int. Cl.
*A61M 5/32* (2006.01)

(52) U.S. Cl. .............. 604/272; 524/494; 524/495

(58) Field of Classification Search ............ 604/272; 524/494, 495
See application file for complete search history.

(56) References Cited

U.S. PATENT DOCUMENTS 5,637,399 A * 6/1997 Yoshikawa et al. ............ 428/369
5,807,914 A * 9/1998 Obayashi et al. ............. 524/267
6,284,831 B1 * 9/2001 Shimpuku et al. ............ 524/494

FOREIGN PATENT DOCUMENTS

| EP | 0 174 011 A2 | 3/1986 |
| JP | 61-62468 A | 3/1986 |
| JP | 62-57565 A | 3/1987 |
| JP | 3-95440 A | 4/1991 |
| JP | 03160052 A * | 7/1991 |
| JP | 06-327772 | 11/1994 |
| JP | 7-303700 A | 11/1995 |
| JP | 10-138244 A | 5/1998 |
| JP | 2005-48009 A | 2/2005 |

OTHER PUBLICATIONS

JP 03160052 A, Jul. 1991, English Abstract.*
Printout of INPADOC Record by Delphion dated Mar. 5, 2008 (corresponds to JP 61-62468 published Mar. 31, 1986).
International Search Report (PCT/ISA/210) dated Dec. 5, 2006.

* cited by examiner

*Primary Examiner* — Satya Sastri
(74) *Attorney, Agent, or Firm* — Buchanan Ingersoll & Rooney PC

(57) ABSTRACT

A medical needle is made of a synthetic resin which is reinforced, including the point part of the needle, to reduce deformation during puncture, even when the needle is produced by injection molding. The needle is made of a synthetic resin composition which includes synthetic resin and reinforcing fiber having a length of 80 μm or below and reinforcing fiber having a length exceeding 80 μm. The number ratio of the former fiber to the whole fiber component is 40% to 90%. A synthetic resin composition for needles includes a synthetic resin and a reinforcing fiber component, wherein the composition is prepared by adding at least two kinds of fibers, namely a fiber having a mean length of 1 mm to 10 mm and a fiber having a mean length of 10 μm to 100 μm to the synthetic resin and kneading the obtained mixture.

9 Claims, 3 Drawing Sheets

SYNTHETIC RESIN NEEDLES AND SYNTHETIC RESIN COMPOSITION FOR NEEDLES

TECHNICAL FIELD

The present invention relates to a needle made of a synthetic resin and a synthetic resin composition for needles. Particularly preferably, the invention relates to a medical needle made of a synthetic resin such as syringe needles, blood sampling needles, retention needles, mixed-injection needles, bottle needles, puncture needles, etc. and a synthetic resin composition for molding the needle made of a synthetic resin.

BACKGROUND ART

As a material for syringe needles used for injection of a liquid drug or sampling of blood, metals such as stainless steel are generally used. The metal-made syringe needles are advantageous in that they can be formed with a thin material thickness, which makes it possible to secure a large flow rate even with a small outside diameter, and that the cutting edge can be polished to be sharp, which permits smooth puncture. The metallic syringe needles, however, cannot be incinerated at the time of disposal thereof, so that they are handed over to a waste collector as they are in their original needle form, to be disposed of by the waste collector. Therefore, there is a request for development of a syringe needle that can be incinerated at the time of disposal, and use of a synthetic resin as a material for such a syringe needle is being investigated. As a material for the synthetic resin-made syringe needles, there is known a material prepared by blending polyphenylene sulfide with wiskers or long fibers to be oriented along the extrusion direction, so as to secure a high strength and an enhanced flexural elastic modulus (refer to, for example, Patent Document 1). Besides, there is known a synthetic resin-made needle in which fibers are present continuously over the whole length of the needle and which is high in strength and is insusceptible to breaking (refer to, for example, Patent Document 2).

In addition, bottle needles used in infusion kits, transfusion kits and the like are used in the state of piercing a rubber stopper or a synthetic resin diaphragm so as to permit flow of a liquid, and they are mostly formed from a synthetic resin which contains reinforcing fibers. In the case of the synthetic resin-made bottle needles, also, it is known that addition of glass fibers is effective in enhancing strength. In relation to the synthetic resin-made bottle needle for piercing a rubber stopper, it is known to use glass fibers or the like so as to reduce the piercing resistance and to enhance the breaking strength (refer to, for example, Patent Documents 3 and 4).

However, in the case of molding a needle while orienting the above-mentioned long fibers along the axial direction, the molding is normally carried out by extrusion, and the sharp needle point part needs secondary working such as cutting and polishing. Besides, when it is attempted to make the needle point sharper for the purpose of making it easier for the bottle needle formed by injection molding to pierce the rubber stopper, the needle part near the point would not readily be loaded with the reinforcing fiber component such as glass fibers. Thus, it has been difficult to reinforce the point part assuredly.

Patent Document 1:
   Japanese Patent Laid-open No. Hei 6-327772
Patent Document 2:
   Japanese Patent Laid-open No. Hei 7-303700
Patent Document 3:
   Japanese Patent Laid-open No. Sho 61-62468
Patent Document 4:
   Japanese Patent Laid-open No. Sho 62-57565

SUMMARY

It is an object of the present invention to provide a needle made of a synthetic resin which is reinforced in its part ranging to its point part and is insusceptible to deformation in puncture even when the needle is one produced by injection molding, and a synthetic resin composition for molding the needle. It is another object of the present invention to provide a needle made of a synthetic resin which ensures that the needle point can be sharpened to have a point radius reduced to or below 30 μm and the sharp needle point can be reinforced so as to mitigate the pain in puncturing the human body with the needle, and a synthetic resin composition for molding the needle.

In order to solve the above-mentioned problems, the present inventor made intensive and extensive studies and, as a result, found out a synthetic resin composition for needles which makes it possible to solve the problems. Based on the finding, the present invention has been attained. More specifically, the present invention has been made based on the finding that, when a needle is formed from a synthetic resin composition admixed with a specified ratio of two kinds of fibers different in mean length, namely, a fiber having an effective length for reinforcement and a fiber having such a length as to permit loading of the needle therewith even in a needle point part, the needle is reinforced even in its point part and shows little dulling or bend even when the needle is a sharp needle produced by injection molding.

Accordingly, the present invention is attained by the following configurations (1) to (9).

(1) A needle made of a synthetic resin, produced by molding a composition which includes a synthetic resin and a reinforcing fiber component, wherein the reinforcing fiber component is included of both a fiber having a length of not more than 80 μm and a fiber having a length of more than 80 μm, and the number ratio of said fiber having a length of not more than 80 μm to the whole fiber component is in the range of 40 to 90%.

(2) A needle made of a synthetic resin as set forth in (1) above, wherein the content of the reinforcing fiber component is 10 to 60 wt %.

(3) A needle made of a synthetic resin as set forth in (1) above, wherein the reinforcing fiber component has a mean fiber diameter of 4 to 23 μm.

(4) A needle made of a synthetic resin as set forth in (1) above, wherein the reinforcing fiber component is selected from among glass fiber and carbon fiber.

(5) A needle made of a synthetic resin as set forth in (1) above, wherein the synthetic resin is selected from the group including thermoplastic resins of polylactic acid, polybutylene succinate, polybutylene adipate, polybutylene succinate-adipate copolymer, polybutylene succinate-carbonate copolymer, polybutylene succinate-polylactic acid copolymer, poly(ε-caprolactone), poly(3-hydroxybutyrate) and its copolymers, polyethylene succinate-terephthalate copolymer, polyethylene succinate-polybutylene succinate-terephthalate copolymer, polybutylene adipate-terephthalate copolymer, polytetramethylene adipate-terephthalate copolymer, polybutylene succinate-adipate-terephthalate copolymer, cyclic olefin resins, polyphenylene sulfide, polyether ether ketone, polybutylene terephthalate, polyethylene terephthalate, polycarbonate, polystyrene, polyamides, polyacetal, modified polyphenylene ether, polyester resins, polytetrafluoroethylene, fluororesins, polysulfone, polyether imides, polyether sulfones, polyether ketones, polyether lactones, liquid crystal polyesters, polyamide imides, polyimides, polyether nitriles, polypropylene, and polyethylene, and mixtures thereof.

(6) A needle made of a synthetic resin as set forth in (1) above, wherein the synthetic resin is selected from the group including polylactic acid, polycarbonates, polystyrene, cyclic olefin resins, polybutylene terephthalate, polyethylene terephthalate, polyether ether ketones, polyether imides, polyphenylene sulfide, and liquid crystal polyester resins.

(7) A needle made of a synthetic resin as set forth in (1) above, which is a medical needle.

(8) A synthetic resin composition for needles which includes a synthetic resin and a reinforcing fiber component, prepared by adding at least two kinds of reinforcing fibers, namely, a fiber having a mean length of 1 to 10 mm and a fiber having a mean length of 10 to 100 μm to the synthetic resin, and kneading the resulting mixture.

(9) A synthetic resin composition for needles as set forth in (8) above, wherein the addition weight ratio of the fiber having a mean length of 1 to 10 mm and the fiber having a mean length of 10 to 100 μm is in the range of from 5:1 to 1:5.

(10) A needle made of a synthetic resin, produced by injection molding of a synthetic resin composition as set forth in (8) above.

According to the present invention, a novel fiber-reinforced synthetic resin composition can be provided, and a needle made of the synthetic resin can be obtained which is reinforced even in the point part and is hardly deformed at the occasion of puncture. Besides, by molding the synthetic resin composition by injection molding or the like, a molded medical needle which is reinforced even in the point part and little deforms in puncturing can be obtained.

BEST MODE FOR CARRYING OUT THE INVENTION

Figure 1:
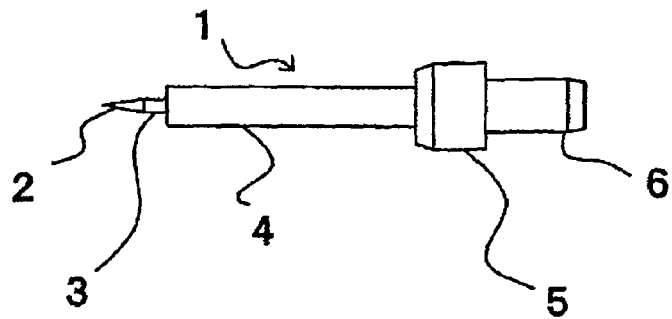
FIG. 1 is a side view of an embodiment of a puncture needle which is a needle made of a synthetic resin according to the present invention.

Now, a synthetic resin composition for needles and a needle made of a synthetic resin which is molded from the synthetic resin composition, according to the present invention, will be described in detail below, based on preferred embodiments.

The resin for use in the synthetic resin composition according to the present invention is not particularly limited. Examples of the resin which can be used include biodegradable resins such as polylactic acid, polybutylene succinate, polybutylene adipate, polybutylene succinate-adipate copolymer, polybutylene succinate-carbonate copolymer, polybutylene succinate-polylactic acid copolymer, poly(ε-caprolactone), poly(3-hydroxybutyrate) and its copolymers, polyethylene succinate-terephthalate copolymer, polyethylene succinate-polybutylene succinate-terephthalate copolymer, polybutylene adipate-terephthalate copolymer, polytetramethylene adipate-terephthalate copolymer, polybutylene succinate-adipate-terephthalate copolymer, etc.

Besides, examples of the resin which can be used in the synthetic resin composition according to the present invention include thermoplastic resins such as cyclic olefin resins, polyphenylene sulfide, polyether ether ketone, polybutylene terephthalate, polyethylene terephthalate, polycarbonate, polystyrene, polyamides, polyacetal, modified polyphenylene ether, polyester resins, polytetrafluoroethylene, fluororesins, polysulfone, polyether imides, polyether sulfones, polyether ketones, polyether lactones, liquid crystal polyesters, polyamide imides, polyimides, polyether nitrites, polypropylene, etc. and mixtures thereof.

The needles made of synthetic resin can be incinerated for disposal, as contrasted to needles made of metal, and ensure easy waste disposal. Particularly, medical needles often undergo adhesion of blood, and, therefore, the needles made of synthetic resin which can be incinerated for disposal have a special effect in the medical field. In addition, where a biodegradable resin is used in the present invention, the resin is decomposed by microorganisms or environmental water, which is preferable in that energy is not consumed needlessly and the burden on the environment is slight.

Further, high-elasticity thermoplastic resins such as polylactic acid, polycarbonate, polystyrene, cyclic olefin resins, polybutylene terephthalate, polyethylene terephthalate, polyether ether ketones, polyether imides, polyphenylene sulfide, liquid crystal polyester, etc. which have a flexural elastic modulus of not less than 2 GPa themselves have a high modulus of elasticity which is preferable for use as needle. Therefore, when such a high-elasticity thermoplastic resin is used to constitute the synthetic resin composition according to the present invention, an excellent needle made of a synthetic resin according to the present invention can be obtained favorably.

The reinforcing fiber component used in the synthetic resin composition according to the present invention is not particularly limited insofar as it enhances the modulus of elasticity of the resin when added to the resin. Examples of the reinforcing fiber component include glass fiber and carbon fiber.

As the carbon fiber for use in the synthetic resin composition according to the present invention, conventionally known various carbon fibers can be used. Specific examples of the carbon fibers which can be used include polyacrylonitrile carbon fiber, pitch carbon fiber, and rayon carbon fiber. The mean diameter of the carbon fiber is preferably 4 to 25 μm, more preferably 6 to 13 μm. In the case of the glass fiber used in the present invention, the mean diameter of the fiber is preferably 4 to 25 μm, more preferably 6 to 13 μm. In both the cases of the carbon fiber and the glass fiber, a mean diameter of less than 4 μm makes it difficult to secure the strength at the needle point, and a mean diameter exceeding 23 μm makes it difficult to load the needle with the fiber component even in the needle point part in molding the needle.

As for the length of the reinforcing fiber component in the synthetic resin composition according to the present invention, the needle made of the synthetic resin needs to contain both a fiber having a length of not more than 80 μm (referred to as short fiber) and a fiber having a length of more than 80 μm (referred to as long fiber). An attempt to produce a needle by adding a reinforcing fiber component to a synthetic resin has hitherto been made, but there has been recognized no analysis that is made paying attention to the length of fiber. The investigations made by the present inventor have elucidated the relationship between the length of the reinforcing fiber component in the synthetic resin composition and the function of the needle.

Specifically, the needle made of a synthetic resin (to be referred to simply as needle) is securely loaded with the short fiber even in its point part, whereby the dulling according to the criterion described later (in the present specification, the phenomenon in which the needle point is slightly collapsed and the point radius is enlarged by about 10% is referred to as "dulling") can be suppressed. If the short fiber alone is added, the rate of breakage or bending (the phenomenon in which the needle point is heavily collapsed and the point radius is enlarged by about 100%) is increased. On the other hand, the long fiber is liable to be oriented along the resin flow direction in molding of the needle, so that the fiber is incorporated in the needle in the state of being oriented in the needle axial direction, whereby the needle part near the needle point can be prevented from breaking or bending. However, the long fiber is hardly incorporated into the needle point part, so that use of the long fiber alone cannot suppress the dulling efficiently, and, hence, the rate of dulling is increased.

Therefore, when the synthetic resin contains both the long fiber and the short fiber, the needle point can be prevented from being deformed. Incidentally, the methods of evaluating the condition where the dulling is slight and the condition where breakage and/or bending is slight will be described later.

When the short fiber in the present invention has a mean length of less then 4 μm, the strength of the needle point can hardly be secured. On the other hand, when the mean length of the short fiber exceeds 80 μm, loading of the needle with the short fiber even in the point part is hardly achieved in molding the needle. Besides, when the long fiber in the present invention has a mean length of 80 μm or below, the strength against breaking or bending can hardly be secured near the needle point. On the other hand, when the mean length of the long fiber exceeds 5 mm, loading of the needle with the long fiber even in the point part is hardly achieved in molding the needle.

In regard of reinforcement of the needle point, the short fiber is incorporated even in the needle point in molding the needle so as to prevent the needle point from dulling in puncture. On the other hand, the long fiber which tends to be oriented in the resin flow direction in molding is incorporated in the needle in the state of being oriented along the needle point direction, so as to prevent breakage and/or bending from occurring near the needle point.

As for the proportions of the short fiber and the long fiber which are contained in the needle point part, the number ratio of the short fiber (the fiber of 80 μm or below in length) to the whole reinforcing fiber component is preferably in the range of 40 to 90%, so as to effectively prevent both the dulling and the breakage or bending of the needle point part in puncturing. A more preferable number ratio is 45 to 85%, and a further preferable number ratio is 50 to 80%.

The synthetic resin composition according to the present invention is prepared by a method in which a mixture of the reinforcing fiber component and the synthetic resin is subjected to melt kneading, or a method in which the reinforcing fiber component is added to a molten synthetic resin and the resulting mixture is kneaded. Therefore, a variety of methods can be adopted for obtaining a distribution of lengths of the reinforcing fibers in the final molded article, and the mean length of the reinforcing fibers before addition is not particularly limited. For efficiently preparing the synthetic resin composition of the present invention, however, it is preferable to add at least two kinds of reinforcing fibers having specified lengths to the composition. Particularly, for obtaining the long fiber fraction as above-mentioned, it is preferable to use chopped strand fibers of the reinforcing fibers having a mean length of not less than 1 mm and less than 10 mm, more preferably a mean length of 3 to 6 mm. This is because the long fiber is cut due to the treatment by a single screw extruder, a twin-screw extruder, a Banbury mixer, rolls, a kneader or the like during the process of adding the reinforcing fiber component to the synthetic resin and kneading the resulting mixture. On the other hand, for obtaining the short fiber fraction as above-mentioned, it is preferable to use milled fibers of the reinforcing fibers having a mean length of 10 to 100 μm, more preferably 20 to 80 μm. This is because the reinforcing fiber added for obtaining the short fiber fraction has, due to the kneading operation, a mean fiber length in the synthetic resin needle which is smaller than that at the time of addition. The reinforcing fibers added to the synthetic resin composition may be surface-treated fibers or fibers with a binding agent adhered thereto.

The addition amount (content) of the reinforcing fiber component in the synthetic resin composition according to the present invention differs depending on the combination of the synthetic resin and the reinforcing fiber component which are adopted. The ratio of the addition amount of the reinforcing fiber component to the whole part of the synthetic resin composition (equal to the content in the synthetic resin-made needle molded from the synthetic resin composition) is generally 10 to 60 wt %, preferably 20 to 50 wt %, and more preferably 30 to 50 wt %. As the addition amount of the fibers is large, it is easier for the needle to be loaded with the fibers even in the needle point part. If the addition amount exceeds the upper limit just-mentioned, however, the mechanical strength of the needle is lowered unfavorably. If the addition amount is below the lower limit, it is impossible to obtain a sufficient strength against dulling and breaking or bending.

The weight ratio of the reinforcing fiber added for obtaining the long fiber fraction to the reinforcing fiber added for obtaining the short fiber fraction is in the range of from about 5:1 to 1:5, preferably from 4:1 to 1:4, more preferably from 3:1 to 1:3. In the method of preparing the synthetic resin composition of the present invention by adding the above-mentioned two kinds of reinforcing fibers, the addition of only the reinforcing fiber added for obtaining the long fiber fraction has the problem that even if the addition amount is increased, a sufficient number of the fibers of the short fiber fraction are not produced, and it is difficult for the needle to be loaded with the reinforcing fibers even in the point part in molding the needle, so that the point part is susceptible to dulling in puncture. When the weight ratio of the reinforcing fiber added for obtaining the long fiber fraction and the reinforcing fiber added for obtaining the short fiber fraction is set in the range of from 5:1 to 1:5, the short fiber is securely incorporated into the needle even in the point part, whereby dulling as well as breakage or bending can be restrained. If the reinforcing fiber added for obtaining the short fiber fraction is added alone, the rate of breakage and/or bending is increased, though the dulling of the needle point upon puncture can be restrained. Therefore, deformation of the needle point can be prevented by adding both the reinforcing fiber added for obtaining the long fiber fraction and the reinforcing fiber added for obtaining the short fiber fraction.

In the synthetic resin composition according to the present invention, one kind or at least two kinds of other thermoplastic resins can be used together in such a range as not to spoil the purpose and effect of the composition. Besides, in order to attain desired characteristics such as enhancement of mechanical strength, enhancement of stability, acceleration of decomposition, antistatic property, enhancement of radiation resistance, etc., known substances generally added to thermoplastic resins may be further blended into the resin composition. Examples of the known substances include talc, antioxidant, heat resisting stabilizer, ultraviolet ray absorber and the like stabilizers, antistatic agent, flame retarder, flame retarding assistant, colorant such as dye and pigment, lubricant, plasticizer, crystallization accelerator, nucleation agent, etc.

The needle made of a synthetic resin according to the present invention allows easy waste disposal, as above-mentioned. Therefore, the needle is particularly suitable for use as a medical needle to which a fluid such as blood and urine is adhered and which is susceptible to infection by virus or bacteria. Examples of the medical needle include: syringe needles used for drug dosing or blood collection from a blood vessel by being mounted to a syringe; blood sampling needles for sampling blood from a blood vessel by being mounted to a syringe or a blood sampling implement; retention needles made to be retained in a blood vessel and used for injecting an infusion or the like; mixed-injection needles used for sampling or injecting a liquid from a mixed-injection part provided in an extracorporeal circulation circuit, an infusion set or a transfusion set; bottle needles provided in an infusion set or a transfusion set and used for connection to an infusion container or a blood container; and puncture needles used for obtaining a small amount of blood by injuring a skin for the purpose of measuring a blood component or the like. Each of these medical needles has a configuration in which its point part has a sharpened shape for piercing a skin or a rubber stopper of a medical implement, and its end part on the opposite side of the point part has a shape such as to permit connection thereof to a syringe, an infusion tube, a puncturing implement or the like. In addition, the needle may be a hollow needle or a solid needle, depending on the purpose of use thereof.

The needle made of a synthetic resin according to the present invention is not limited to the above-mentioned medical needle, and may naturally be a commonly used needle such as a fishing hook, a sewing needle, etc. In this case, also, the characteristic feature permitting easy waste disposal exhibits a sufficient effect.

As a molding method for the needle made of a synthetic resin according to the present invention, any of known resin molding methods can be adopted. Examples of the molding method which can be used include: a method in which raw materials including the synthetic resin, the reinforcing fiber component, and optional additives and the like are placed in a kneading machine such as a single screw extruder, a twin-screw extruder, a Banbury mixer, rolls, a kneader, etc., then the raw materials are subjected to melt kneading, and the kneaded mixture is molded by supplying it into a molding machine such as an injection molding machine, an extruder, a compression molding machine, a blow molding machine, etc.; a method in which the raw materials are pre-mixed, followed by placing in the molding machine, melt kneading, and molding; and a method in which the raw materials are supplied into the molding machine, and molding is carried out while performing melt blending. Among others, injection molding by an injection molding machine may be applied to the synthetic resin composition according to the present invention, whereby the composition can be molded into the final needle shape without need for any after-treating step, and an enhanced productivity is realized.

Now, the present invention will be described more in detail below referring to non-limitative working examples.

EXAMPLES

Preparation Examples of Synthetic Resin Compositions

Polylactic acid (Terramac TE-8300, produced by Unitika Ltd.), chopped strand glass fibers (Chopped Strand, having a mean diameter of 6 μm and a mean length of 3 mm, produced by Asahi Fiber Glass Co., Ltd.) and milled glass (Milled Fiber, having a mean diameter of 10 μm and a mean length of 60 μm, produced by Asahi Fiber Glass Co., Ltd.) were blended in each of the compositions (the numerical values are in wt %) in Examples 1, 2, 3 and Comparative Examples 1, 2, 3 shown in Table 1, then the blends were pelletized by kneading at 180° C. using a twin-screw extruder.

Production Examples of Puncture Needles

The pellets as described in the paragraph of <Preparation Examples of Synthetic Resin Compositions> above were respectively placed in a puncture needle mold having a shape conforming to a commercially available puncturing implement (Medisafe Finetouch MS-GN02, produced by Terumo Corporation), and injection molding was conducted at a cylinder temperature of 210° C. and a mold temperature of 110° C., to obtain puncture respective needles as shown in FIG. 1 (the needles had a conical shape with a point angle of 20° and a point radius of 15 μm). The puncture needle 1 shown in FIG. 1 has a structure in which a needle point part 2, a needle 3, a trunk part 4, a needle hub 5 and a connector part 6 are continuously arranged sequentially in the axial direction. In addition, the puncture needle 1 is entirely covered with a housing (not shown), which is provided with a tip opening through which the needle point part 2 can protrude and a rear end opening where the connector part 6 can be connected to the puncturing implement. The connector part 6 is connected to a puncturing mechanism member (not shown) of the puncturing implement, and, when the puncturing implement is put into a puncturing operation, the puncture needle is moved toward a skin to be punctured. The needle hub 5 and the trunk part 4 hold the puncture needle 1 inside the housing in such a manner that the puncture needle 1 can be moved in the axial direction. The length by which the needle point part 2 protrudes from the tip opening by shooting by the puncturing implement is the puncture depth of the puncture needle 1.

<Evaluation of Puncture with Puncture Needle>

Each of the puncture needles was attached to the commercially available puncturing implement (Medisafe Finetouch MS-GN02, produced by Terumo Corporation), and was made to pierce a silicone rubber (hardness: 48, thickness: 5 mm) with a puncture depth of 4 on a puncture depth scale (puncture depth: 1.8 mm). The needle point radius was measured before and after puncture, and the deformation ratio of the needle point was calculated by the formula shown below. For each of the synthetic resin compositions, six puncture needles were served to evaluation, and the presence or absence of deformation was judged by use of the criterion shown below. The results are given in Table 1.

Deformation Ratio (%)=Needle point radius (μm) after puncture/Needle point radius (μm) before puncture×100

Criterion for Judgment

Little dulling: Deformation ratio≦110%

No breakage or bend: Deformation ratio≦200%

TABLE 1

|  |  | Example 1 | Example 2 | Example 3 | Comparative Example 1 | Comparative Example 2 | Comparative Example 3 |
|---|---|---|---|---|---|---|---|
| Resin | Polylactic acid | 60 | 60 | 60 | 60 | 70 | 100 |
| Glass fiber | Chopped strand | 30 | 20 | 10 | 40 | 0 | 0 |
|  | Milled fiber | 10 | 20 | 30 | 0 | 30 | 0 |
| Evaluation of puncture | Little dulling | 2/6 | 4/6 | 2/6 | 0/6 | 1/6 | 0/6 |
|  | No breakage or bend | 4/6 | 6/6 | 4/6 | 4/6 | 2/6 | 0/6 |

(Numerical values of addition ratio are in wt %)

<Composition Analysis of Fibers in Needle Point Part>

Figure 2:
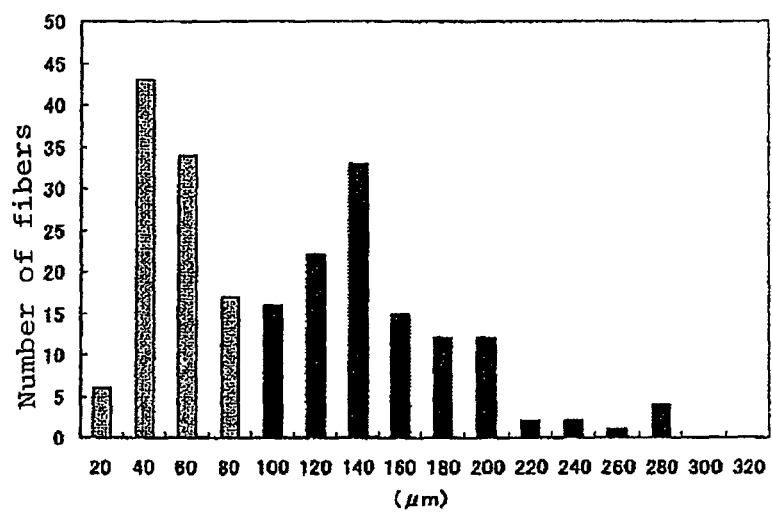
FIG. 2 is a graph showing the distribution of lengths of reinforcing fibers contained in the puncture needle of Example 1 which is an embodiment of the present invention.
Figure 3:
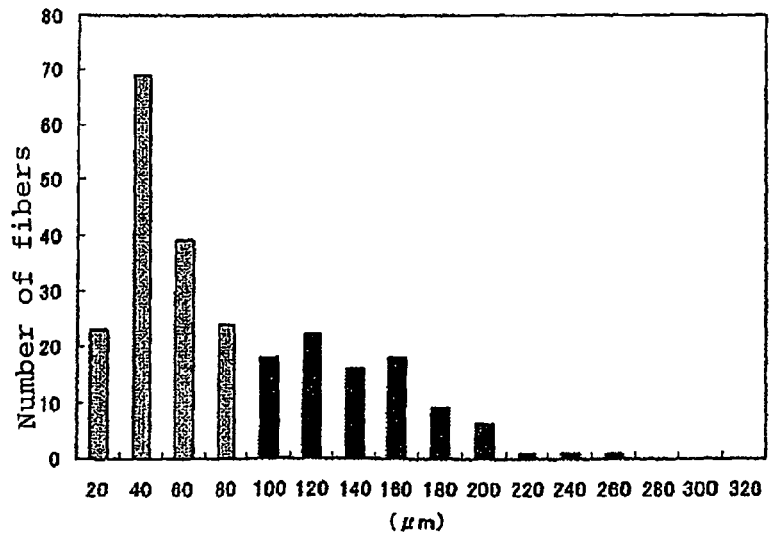
FIG. 3 is a graph showing the distribution of lengths of reinforcing fibers contained in the puncture needle of Example 2 which is an embodiment of the present invention.
Figure 4:
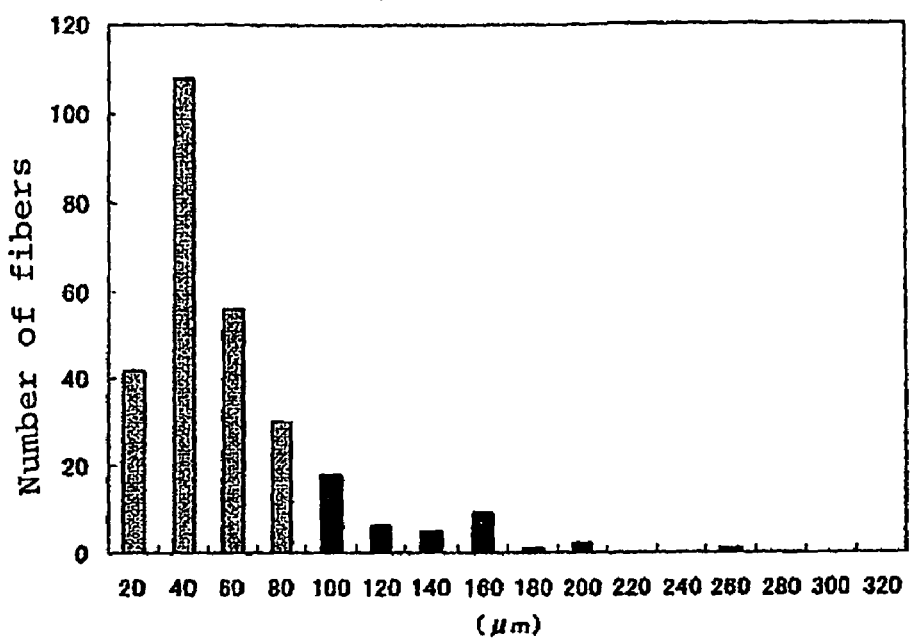
FIG. 4 is a graph showing the distribution of lengths of reinforcing fibers contained in the puncture needle of Example 3 which is an embodiment of the present invention.
Figure 5:
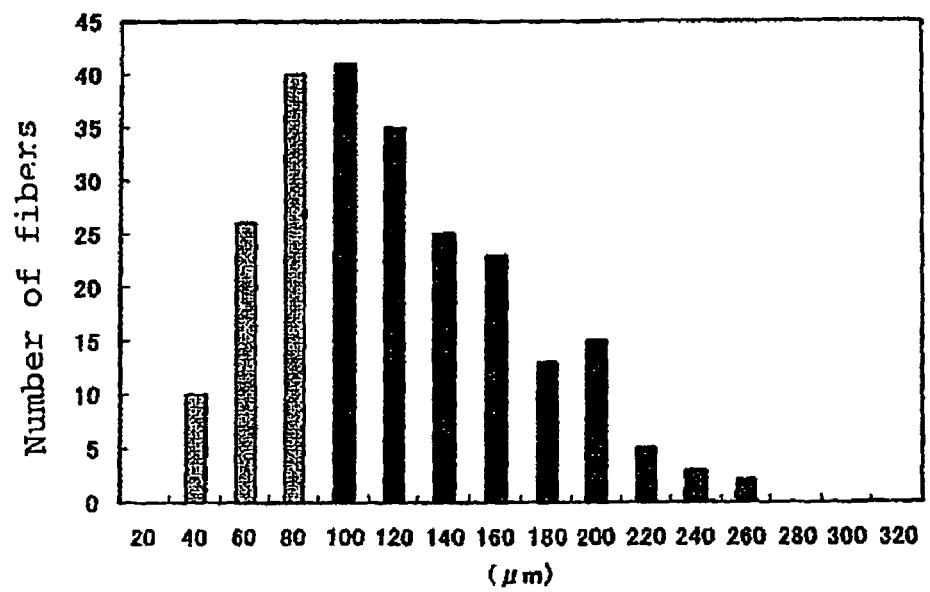
FIG. 5 is a graph showing the distribution of lengths of reinforcing fibers contained in the puncture needle of Comparative Example 1 which is a comparative embodiment of the present invention.
Figure 6:
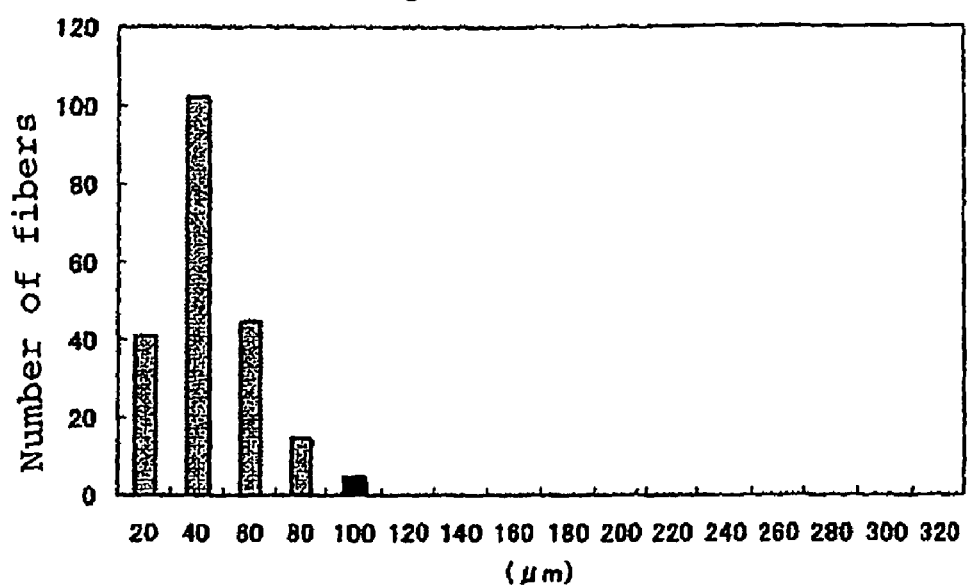
FIG. 6 is a graph showing the distribution of lengths of reinforcing fibers contained in the puncture needle of Comparative Example 2 which is a comparative embodiment of the present invention.

A point part of each of the puncture needles in Example 1 was cut off, and was hot pressed (temperature: 220° C., pressure: 3 MPa) to produce a thin film. The thin film was observed under a microscope, to measure the lengths and the number of glass fibers present in an area of 0.5 mm×0.5 mm. An analysis of the distribution of lengths of the glass fibers revealed that the glass fiber component was composed of a fiber having a length of 80 µm or below and a fiber having a length exceeding 80 µm, and the number ratio of the former fiber to the whole fiber component was 46% (FIG. 2).

In the same manner as above, the needles produced respectively in Examples 2, 3 and Comparative Examples 1, 2 were analyzed. As a result, the number ratios of the former fiber to the whole fiber component were 63%, 84%, 32%, and 98%, respectively (FIGS. 3 to 6). Incidentally, the numerical values on the axis of abscissas indicate the upper limits; for example, where the numerical value is "80", the fibers include those fibers which are more than 60 µm and not more than 80 µm in length. Besides, in Examples of the present invention, the glass fibers measured were not less than 4 µm in length.

As shown in Table 1 and FIGS. 2 to 6, Examples 1, 2, 3 in which the number ratio of the fiber having a length of 80 µm or below to the whole fiber component was in the range of 40 to 90% gave less dulling and less breakage or bend, as compared with Comparative Examples. In Comparative Example 1 in which the number ratio of the fiber having a length of 80 µm or below to the whole fiber component was 32%, satisfactory performance could not obtained because the rate of dulling was high, though the breakage and/or bend was little. In Comparative Example 2 in which the number ratio of the fiber having a length of 80 µm or below to the whole fiber component was 98%, the performance as to breakage and/or bend was poor, through a slight improving effect on dulling was observed. In Comparative Example 3 in which no reinforcing fiber component was contained in the resin composition, the product could not at all used as a puncture needle.

<Production of Synthetic Resin Compositions and Puncture Needles>

By use of a polystyrene (GP XC-510A, produced by Dainippon Ink And Chemicals, Inc.), a cyclid olefin resin (Zeonex 690R, produced by Zeon Corporation) and a polyphenylene sulfide (Fortron 0220A9, produced by Polyplastics Co., Ltd.) as synthetic resins with resin and a fiber ratio similar to those in the preparation example of the synthetic resin composition in Example 2, pellets of synthetic resin compositions in Examples 4, 5, 6 and Comparative Examples 4, 5, 6 according to the compositions as shown in Table 2 were prepared. By use of the puncture needle mold mentioned above, injection molding was conducted to obtain respective puncture needles (each of the needles had a conical shape with a point angle of 20° and a point radius of 15 µm).

<Evaluation of Puncture with Puncture Needles>

Each of the puncture needles was attached to the commercially available puncturing implement (Medisafe Finetouch MS-GN02, produced by Terumo Corporation), and was made to pierce a silicone rubber (hardness: 48, thickness: 5 mm) with a puncture depth of 4 on puncture depth scale (puncture depth: 1.8 mm). The needle point radius was measured before and after puncture, and the deformation ratio was calculated according to the same criterion for evaluation as that in Examples 1 to 3. For each of the synthetic resin compositions, six puncture needles were served to the evaluation. The results are given in Table 2.

TABLE 2

|  |  | Example 4 | Example 5 | Example 6 | Comparative Example 4 | Comparative Example 5 | Comparative Example 6 |
|---|---|---|---|---|---|---|---|
| Resin | Kind | Polystyrene | Cyclic olefin resin | Polyphenylene sulfide | Polystyrene | Cyclic olefin resin | Polyphenylene sulfide |
|  | Addition amount | 60 | 60 | 60 | 100 | 100 | 100 |
| Glass fiber | Chopped strand | 20 | 20 | 20 | 0 | 0 | 0 |
|  | Milled fiber | 20 | 20 | 20 | 0 | 0 | 0 |
| Evaluation of puncture | Little dulling | 5/6 | 5/6 | 5/6 | 0/6 | 0/6 | 0/6 |
|  | No breakage or bend | 6/6 | 6/6 | 6/6 | 0/6 | 0/6 | 0/6 |

(Numerical values of addition ratio are in wt %)

As shown in Table 2, also in the cases of using the polystyrene, the cyclic olefin resin and the polyphenylene sulfide, the puncture needles produced from a synthetic resin composition loaded with the two kinds of reinforcing fibers differing in fiber length showed little dulling as well as little breakage and/or bend.

<Production of Synthetic Resin Compositions and Puncture Needles>

By use of chopped strand glass fibers (Chopped Strands (mean diameter: 6 μm, mean length 6 mm), (mean diameter: 6 μm, mean length 3 mm), (mean diameter: 10 μm, mean length 3 mm), and (mean diameter: 13 μm, mean length 3 mm), produced by Asahi Fiber Glass Co., Ltd.) and a milled glass (Milled Fiber (mean diameter: 10 μm, mean length: 60 μm), produced by Asahi Fiber Glass Co., Ltd.) as fibers with resin and a fiber ratio similar to those in the preparation example of the synthetic resin composition in Example 2, pellets of synthetic resin compositions having the compositions shown in Table 3 were prepared. By use of the above-mentioned puncture needle mold, injection molding was conducted to obtain puncture needles in Examples 7, 8, 9 (the needle had a conical shape with a point angle of 20° and a point radius of 15 μm).

<Evaluation of Puncture with Puncture Needles>

Each of the puncture needles was attached to the commercially available puncturing implement (Medisafe Finetouch MS-GN02, produced by Terumo Corporation), and was made to pierce a silicone rubber (hardness: 48, thickness: 5 mm) with a puncture depth of 4 on puncture depth scale (puncture depth: 1.8 mm). The needle point radius was measured before and after puncture, and the deformation ratio was calculated according to the same criterion for evaluation as in Examples 1 to 3. For each of the synthetic resin compositions, six puncture needles were served to the evaluation. The results are shown in Table 3.

TABLE 3

| | | Example 7 | Example 8 | Example 9 |
|---|---|---|---|---|
| Resin | Polylactic acid | 60 | 60 | 60 |
| Glass fiber | Chopped strand | (Diameter: 6 μm, Length: 6 mm) 20 | (Diameter: 10 μm, Length: 3 mm) 20 | (Diameter: 13 μm, Length: 3 mm) 20 |
| | Milled fiber | (Diameter: 10 μm, Mean length: 60 μm) 20 | (Diameter: 10 μm, Mean length: 60 μm) 20 | (Diameter: 10 μm Mean length: 60 μm) 20 |
| Evaluation of puncture | Little dulling | 4/6 | 4/6 | 3/6 |
| | No breakage or bend | 6/6 | 6/6 | 6/6 |

(Numerical values of addition ratio are in wt %)

As shown in Table 3, the puncture needles produced from a synthetic resin composition loaded with two kinds of reinforcing fibers, one having a mean length of 1 to 10 mm and the other having a mean length of 10 to 100 μm, with the mean fiber diameter of the reinforcing fibers being 4 to 23 μm, showed little dulling as well as no breakage or bend.

The invention claimed is:

1. A needle made of a composition comprising synthetic resin and a reinforcing fiber component, wherein the needle comprises a needle point having a point radius of 30 μm or below, the reinforcing fiber component comprising both fibers having a length of not more than 80 μm and fibers having a length of more than 80 μm, and a ratio of the fibers having a length of not more than 80 μm to a total amount of the fiber component is 40% to 90%.

2. The needle as set forth in claim 1, wherein the reinforcing fiber component is 10% to 60 wt % of the composition forming the needle.

3. The needle as set forth in claim 1, wherein the reinforcing fiber component has a mean fiber diameter of 4 to 23 μm.

4. The needle as set forth in claim 1, wherein the fibers in the reinforcing fiber component are glass fibers or carbon fibers.

5. The needle as set forth in claim 1, wherein said synthetic resin is selected from the group consisting of thermoplastic resins of polylactic acid, polybutylene succinate, polybutylene adipate, polybutylene succinate-adipate copolymer, polybutylene succinate-carbonate copolymer, polybutylene succinate-polylactic acid copolymer, poly(ε-caprolactone), poly(3-hydroxybutyrate) and its copolymers, polyethylene succinate-terephthalate copolymer, polyethylene succinate-polybutylene succinate-terephthalate copolymer, polybutylene adipate-terephthalate copolymer, polytetramethylene adipate-terephthalate copolymer, polybutylene succinate-adipate-terephthalate copolymer, cyclic olefin resins, polyphenylene sulfide, polyether ether ketone, polybutylene terephthalate, polyethylene terephthalate, polycarbonate, polystyrene, polyamides, polyacetal, modified polyphenylene ether, polyester resins, polytetrafluoroethylene, fluororesins, polysulfone, polyether imides, polyether sulfones, polyether ketones, polyether lactones, liquid crystal polyesters, polyamide imides, polyimides, polyether nitriles, polypropylene, and polyethylene, and mixtures thereof.

6. The needle as set forth in claim 1, wherein the synthetic resin is selected from the group consisting of polylactic acid, polycarbonates, polystyrene, cyclic olefin resins, polybutylene terephthalate, polyethylene terephthalate, polyether ether ketones, polyether imides, polyphenylene sulfide, and liquid crystal polyester resins.

7. The needle as set forth in claim 1, wherein the needle is a medical needle.

8. The needle as set forth in claim 1, wherein the ratio of the fibers having the length of not more than 80 μm to the total amount of the fiber component is 50% to 80%.

9. The needle as set forth in claim 1, wherein the synthetic resin is a biodegradable resin.

* * * * *